(12) United States Patent
Holman et al.

(10) Patent No.: US 8,454,681 B2
(45) Date of Patent: Jun. 4, 2013

(54) BIFURCATION DELIVERY SYSTEMS AND METHODS

(75) Inventors: Tom Holman, Minneapolis, MN (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1401 days.

(21) Appl. No.: 11/520,920

(22) Filed: Sep. 13, 2006

(65) Prior Publication Data

US 2008/0065141 A1    Mar. 13, 2008

(51) Int. Cl.
  *A61F 2/06*    (2006.01)
(52) U.S. Cl.
  USPC ........ 623/1.35; 623/1.11; 623/1.12; 606/108; 606/191; 606/194
(58) Field of Classification Search
  USPC ............... 623/1.11, 1.35, 1.12; 606/108, 191, 606/194
  See application file for complete search history.

(56) References Cited

U.S. PATENT DOCUMENTS

| | | | |
|---|---|---|---|
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 7,220,275 B2 | 5/2007 | Davidson et al. | |
| 2004/0138737 A1 | 7/2004 | Davidson et al. | |
| 2004/0176837 A1 | 9/2004 | Atladottir et al. | |
| 2005/0015108 A1 | 1/2005 | Williams et al. | |
| 2005/0102019 A1* | 5/2005 | Yadin | 623/1.11 |
| 2005/0187602 A1 | 8/2005 | Eidenschink | |
| 2006/0106448 A1* | 5/2006 | Shaked | 623/1.11 |
| 2006/0259116 A1* | 11/2006 | Feld et al. | 623/1.11 |
| 2007/0100301 A1* | 5/2007 | Gumm | 604/284 |
| 2007/0203562 A1 | 8/2007 | Malewicz et al. | |
| 2008/0171975 A1 | 7/2008 | Jennings et al. | |

FOREIGN PATENT DOCUMENTS

| | | |
|---|---|---|
| EP | 1 475 054 A2 | 11/2004 |
| WO | WO 00/48517 | 8/2000 |
| WO | WO 01/74273 A1 | 10/2001 |
| WO | WO 02/068012 A2 | 9/2002 |
| WO | WO 2006/053106 A1 | 5/2006 |

* cited by examiner

*Primary Examiner* — Gary Jackson
*Assistant Examiner* — Kevin Everage
(74) *Attorney, Agent, or Firm* — Seager, Tufte & Wickhem, LLC

(57) ABSTRACT

A catheter assembly including a side branch locator that is moveable between a retracted position within a main vessel of a vessel bifurcation, and an extended position wherein a distal end of the side branch locator extends into a branch vessel of the vessel bifurcation. The side branch locator includes a first end fixed relative to a portion of the catheter assembly that remains in the main vessel. A second end of the side branch locator is moveable between the retracted and extended positions. The catheter assembly can include a moveable sheath that holds the side branch locator in the retracted position. The catheter assembly can further include a stent having a lateral branch opening through which the side branch locator extends.

10 Claims, 6 Drawing Sheets

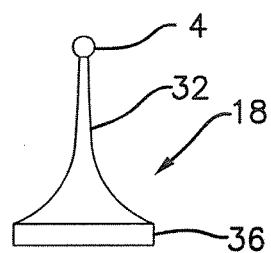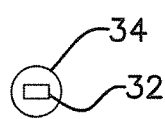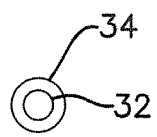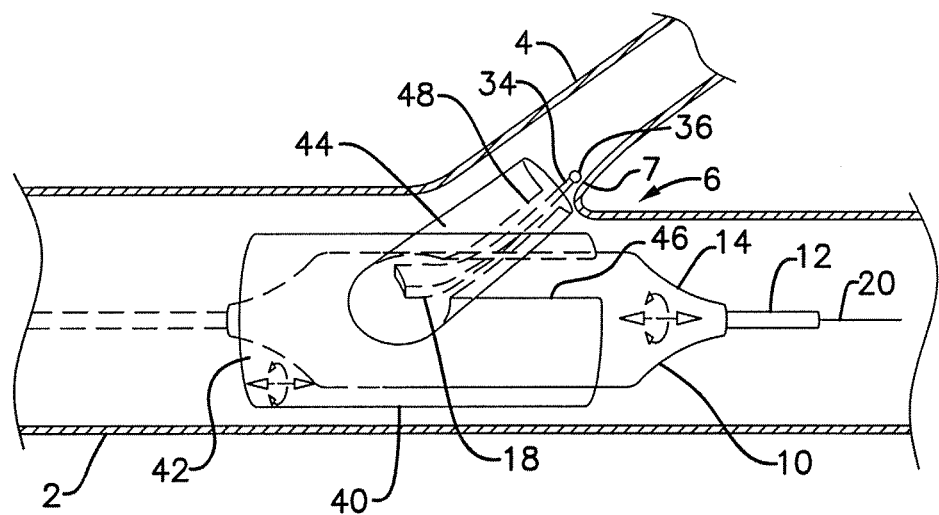

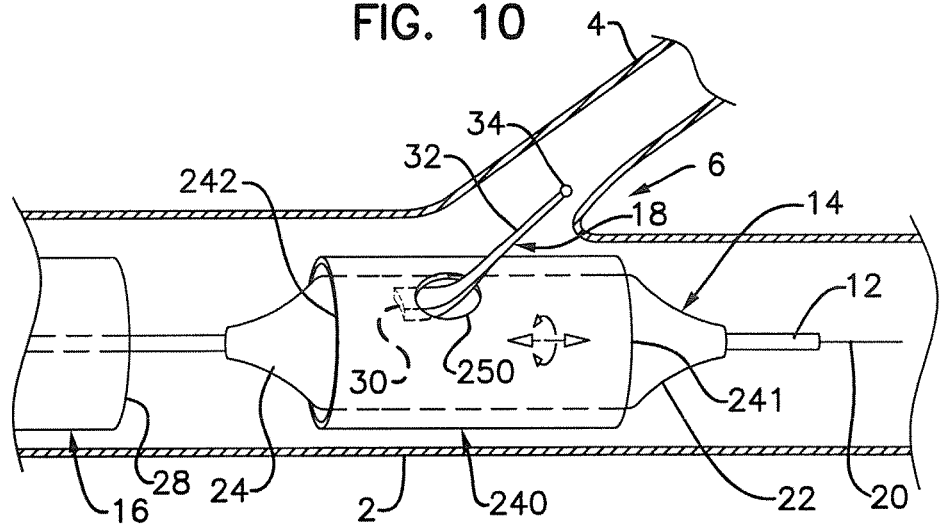
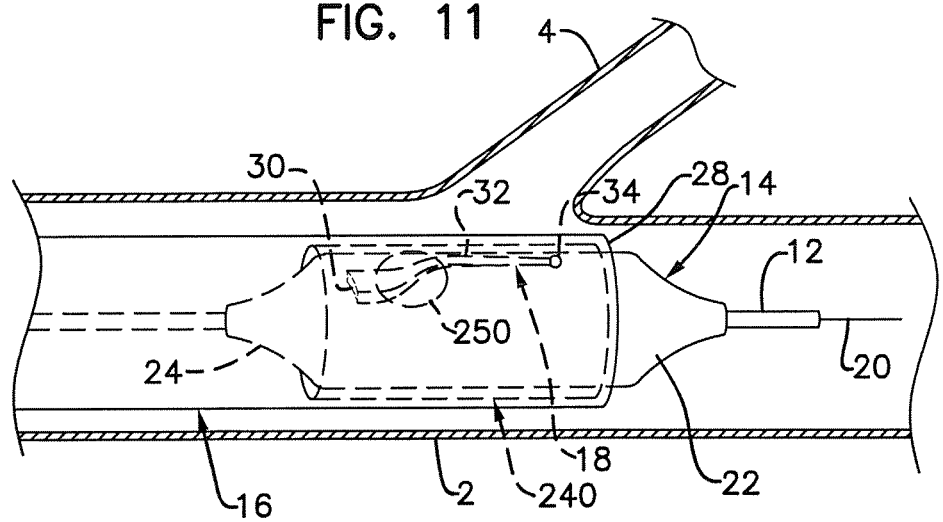

BIFURCATION DELIVERY SYSTEMS AND METHODS

TECHNICAL FIELD

This disclosure generally relates to bifurcation treatment systems and related methods of treating bifurcated lumens in a patient. Preferred arrangements provide for catheter assemblies used to orient the bifurcation treatment system relative to a branch vessel of a vessel bifurcation.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vessel or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall, and treating dissections in blood vessel walls caused by balloon angioplasty of coronary arteries.

While conventional stent technology is relatively well developed, stent technologies related to treatment of the region of a vessel bifurcation are still being developed.

SUMMARY OF THE DISCLOSURE

The present disclosure generally relates to a catheter assembly for treatment of a vessel bifurcation. The catheter assembly includes a side branch locator that is moveable between a first position within a main vessel of the vessel bifurcation, and an extended position wherein a distal end of the side branch locator is positioned within a branch vessel of the vessel bifurcation. The side branch locator includes a first end fixed relative to a portion of the catheter assembly that remains in the main vessel. A second end of the side branch locator is moveable between the first position and the extended position.

The side branch locator can be held in the first position using different types of structures and constructions. For example, the catheter assembly can include a sheath that surrounds the side branch locator to hold the side branch locator in the first position. The sheath is moveable between a position surrounding the side branch locator member, and a proximally retracted position wherein a distal end of the sheath is positioned proximally of the locator member.

The catheter assembly can further include a stent positioned around the side branch locator. The stent can include a lateral branch opening in a sidewall of the stent at a location between distal and proximal open ends of the stent. The side branch locator can extend through the lateral branch opening of the stent and into the branch vessel to align the lateral branch opening relative to the branch vessel.

There is no requirement that an arrangement include all features characterized herein to obtain some advantage according to this disclosure.

BRIEF DESCRIPTION OF THE DRAWINGS

FIG. 4 is a schematic cross-sectional view of the side branch locator taken along indicators 4-4 in FIG. 4.

FIG. 5 is another schematic cross-sectional view of the side branch locator taken along indicators 5-5 in FIG. 4.

FIG. 6 is a schematic representation of an example stent surrounding the bifurcation delivery system shown in FIG. 3.

FIG. 10 is a schematic representation of a bifurcation delivery system with a side branch locator extending through a sidewall opening in the stent and the sheath retracted to permit the side branch locator to move into a deployed state.

FIG. 11 is a schematic representation of the bifurcation delivery system shown in FIG. 10 with the sheath positioned to hold the side branch locator in a non-deployed state.

DETAILED DESCRIPTION

I. General Background

Figure 1:
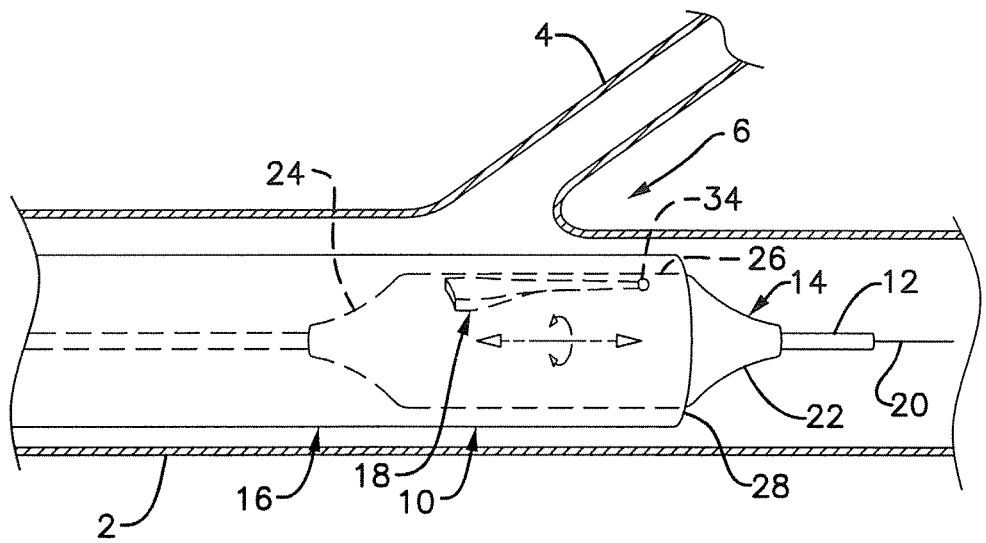
FIG. 1 is a schematic representation of a bifurcation delivery system constructed according to principles of this disclosure and positioned adjacent a vessel bifurcation.

This disclosure relates to bifurcation treatment systems and related methods of treating bifurcations in a patient's body. The term bifurcation means a division location from one unit into two or more units. Generally, two types of bifurcations of a body organ include 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel). The term conduit means a channel (e.g., a pipe or tube) through which something such as a fluid is conveyed. The terms lumen and conduit are used interchangeable throughout this document.

An example bifurcation is a vessel bifurcation that includes a continuous main vessel and a branch vessel, wherein the vessels define a main lumen and a branch lumen, respectively that are in fluid communication with each other. A vessel bifurcation can alternatively include a parent vessel that divides into first and second branch vessels, wherein the vessels define a parent lumen and first and second branch lumens, respectively, which lumens are all in fluid communication with each other. Example applications of the inventive principles disclosed herein include bifurcation treatment systems for use in cardiac, coronary, renal, peripheral vascular, gastrointestinal, pulmonary, urinary, and neurovascular systems.

The example bifurcation treatment systems disclosed herein are useful for aligning features of the bifurcation treatment system relative to a branch vessel of the vessel bifurcation. For example, the example bifurcation treatment systems can be used for alignment of a stent relative to a branch vessel when the stent is positioned in the main vessel of the vessel bifurcation. An example bifurcation treatment system includes a catheter shaft, an inflatable member mounted to the catheter shaft, and a side branch locator positioned on the inflatable member. The example system can also include a sheath. The sheath is moveable relative to the balloon expandable member to enclose and release the distal end of the side branch locator relative to an interior of the sheath.

The example treatment systems can be used with a guidewire that extends within the main vessel to the vessel bifurcation. The catheter shaft of the bifurcation treatment system typically includes a guidewire lumen sized to receive the guidewire. The catheter shaft also includes an inflation lumen adapted to provide inflation fluid to the inflatable member. The guidewire lumen and inflation lumen can extend co-linearly (e.g., side-by-side) or coaxially.

The bifurcation treatment systems disclosed herein can further include a stent. The bifurcation treatment systems can be adapted to position the stent at a bifurcation treatment site. A variety of stents can be used with the bifurcation treatment systems disclosed herein. Examples of such stents can be found in, for example, in U.S. Pat. Nos. 6,210,429 and 6,325,826 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located on a sidewall of the stent at a location between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main vessel of the vessel bifurcation with the lateral branch opening aligned with an opening into the branch vessel. Alignment of the lateral branch opening with the opening into the branch vessel includes requires radial and axial alignment. The stent, including the expandable structure surrounding the lateral branch opening, can be expanded with a single expansion or multiple expansions using one or more inflatable balloons.

The stents can alternatively include a branch extension that extends away from a main body of the stent. The branch extension can extend at an angle relative to the main body. The stent can include a slot that extends from a distal end of the main body proximally to an intersection point between the branch extension and the main body of the stent, and from the intersection point to a distal end of the branch extension. The first and second portions are aligned to provide a continuous opening in the stent between the distal end of the branch extension and the distal end of the main body of the stent. The slot permits the stent to advance over the side branch locator when the side branch locator is extended into the branch vessel of the vessel bifurcation.

Typically, the stent is expanded once it is properly positioned in the main vessel with the sidewall opening of the stent or the branch extension of the stent aligned with the branch vessel. The stent can be expanded with a single expansion. Alternatively, multiple expansions can be used to expand the stent. In some embodiments, more than one expandable balloon member can be used to expand the stent.

In general, a wide variety of stents, balloon expandable members, sheaths, guidewires, and branch locator configurations can be used with the bifurcation treatment system embodiments of the present disclosure and should not be limited to any particular design or configuration.

One aspect of the examples disclosed herein relates to the anchoring and resistance to torsion provided by the side branch locator during inflation of the inflatable balloons of the bifurcation delivery system. An inflation balloon in a deflated stated is typically folded over itself to reduce the outer profile of the balloon for purposes of passing through a vessel. Typically, the balloon tends to rotate during inflation of the balloon. The example side branch locators disclosed herein, when positioned at least partially within a branch vessel, help maintain radial alignment of the bifurcation delivery system relative to the branch vessel as the balloon inflates. The locator counters the torque forces applied by the inflating balloon to maintain the relative alignment with the branch vessel. If a side opening of the stent being expanded by the inflation balloon is positioned encircling the side branch locator, the anchoring of the side branch locator will improve alignment of the side opening of the stent with the ostium of the branch vessel.

II. The Example Illustrated in FIGS. 1-9

An illustrated view of an example bifurcation treatment system 10 is shown with reference to FIGS. 1-9. FIG. 1 illustrates the system 10 positioned within a main vessel 2 adjacent to the ostium of a branch vessel 4. The general area of separation of branch vessel 4 from main vessel 2 is defined as a vessel bifurcation 6. In accordance with an alternative definition, that portion of main vessel 2 proximal of bifurcation 6 can be referred to as a parent or first vessel, that portion of main vessel 2 distal of the bifurcation 6 can be referred to as a first branch vessel, and the branch vessel 4 can be referred to as a second branch vessel. The bifurcation delivery system 10 generally comprises a catheter shaft 12, an inflatable balloon 14, a sheath 16, a side branch locator 18, and a guidewire 20. The main catheter member can define or include other structure that defines one or more internal lumens for passage of the guidewire 20 (e.g., a guidewire lumen (not shown)) and for delivery of inflation fluid to the inflatable balloon 14.

Figure 1A:
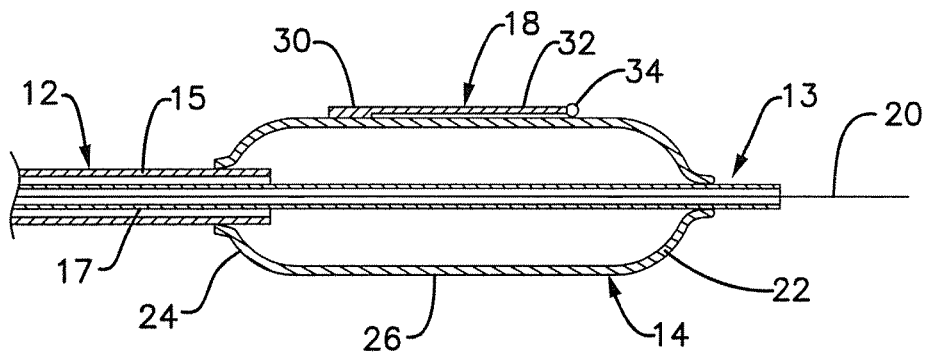
Figure 1B:
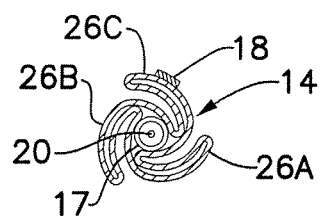

The inflatable balloon 14 is positioned at a distal end 13 of the catheter shaft 12 (see FIG. 1A). Inflatable balloon 14 includes distal and proximal ends 22, 24 and an inflatable body 26. The proximal end 24 of the inflatable balloon 14 is secured to an inflation lumen 15 of the catheter shaft 12. The distal end 22 is secured to a guidewire lumen 17 of the catheter shaft. The guidewire 20 extends through the guidewire lumen 17. The inflation lumen 15 is used to inflate and deflate the inflatable body 26 of the inflation lumen. Prior to inflation, the inflatable balloon 14 is arranged with a plurality of folds 26a, 26b, 26c (see FIG. 1B) that reduce the outer profile of the bifurcation delivery system 10 for purposes of passing the bifurcation delivery system through a vessel.

The side branch locator 18 is mounted to the inflatable body 26 between the distal and proximal ends 22, 24. The side branch locator 18 is shown positioned on an outer surface of the inflatable body 26 at an axial location between ends 22, 24. The side branch locator 18 includes a base 30, a radially moveable arm 32, and a distal tip 34. The base 30 is secured to the inflatable body 26 while the moveable arm 32 and distal tip 34 are not directly secured to the inflatable body 26. The moveable arm 32 and distal tip 34 are moveable relative to the inflatable body 26. Example types and direction of movement of the moveable arm 32 and distal tip 34 are described below.

Figure 2:
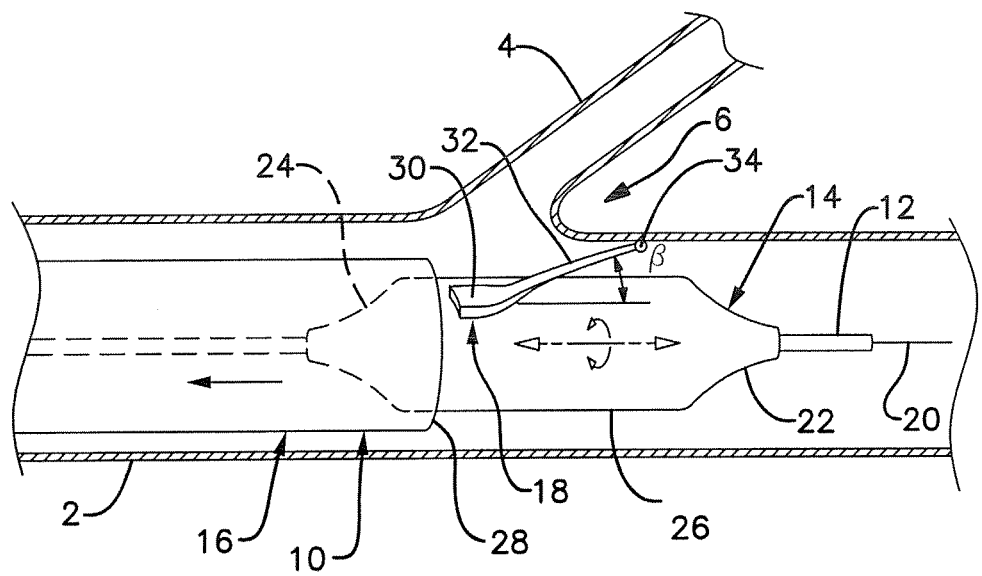
FIG. 2 is a schematic representation of the bifurcation delivery system shown in FIG. 1 with a side branch locator deployed within a main vessel branch.

In the illustrated example, the sheath 16 is axially moveable relative to the inflatable balloon 14. The sheath 16 can move at least between a first position covering the side branch locator 18 (see FIG. 1) and a second position wherein the side branch locator 18 is released and able to move into an extended position (see FIG. 2). The sheath 16 can also be moveable between the second position shown in FIG. 2 and the first position shown in FIG. 1 to recapture the side branch locator 18 within the sheath 16. When the side branch locator 18 is released as shown in FIG. 2, the side branch locator 18 can be used to orient the system 10 relative to the branch vessel 4 as will be described in further detail below.

The sheath 16 can be structured as a continuous elongate tubular member between a distal end 28 and a proximal end (not shown) positioned outside of the patient. The proximal end of the sheath 16 can be pushed and pulled to change a position of the distal end 28 relative to the side branch locator 18. The cross-sectional size and shape of the sheath 16 can vary between the proximal and distal ends. For example, the cross-sectional size of the sheath 16 can be sized at the distal end 28 to pass over the inflatable balloon when in a deflated state and the side branch locator 18 when in a first position (also referred to as a restrained position) as shown in FIG. 1, while other portions of the sheath 16 proximal of the distal end 28 have a smaller cross-sectional size.

In alternative examples, the sheath 16 includes a tubular portion at a distal end and a pull wire connected to the tubular portion that is exposed at a proximal end for axial adjustment of the sheath by the physician. The tubular portion in this example typically has a length greater than a length of the side branch locator 18 and less than a total length of the sheath 16. The tubular portion can alternatively have a length less than a length of the inflatable balloon 14 and greater than a length of the moveable arm 32. A proximal end of the pull wire extends proximally outside of the patient. The guidewire can be pushed and pulled to change a position of the sheath 16 relative to the side branch locator 18.

The inflatable balloon 14 can have varied shapes and sizes and can be constructed of any suitable material. The inflatable balloon 14 and all other balloons disclosed herein can be made of any suitable balloon material including compliant and non-compliant materials and combinations thereof. The catheter shaft 12 and other catheter portions disclosed herein can also comprise any suitable material. Some example materials for the inflatable balloon and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

The catheter shaft 12 includes an inflation lumen 15 (see FIG. 1A) adapted to supply pressurized inflation fluid to the balloon 14 for inflation of the balloon 14. The inflation lumen can also be used to drain inflation fluid from the balloon 14 when deflation of the balloon 14 is required. The balloon 14 is initially deflated when the bifurcation delivery system 10 is advanced along the guidewire 20 to the vessel bifurcation 6. After the bifurcation delivery system 10 has been properly oriented radially and axially relative to the branch vessel 4 using, for example, the side branch locator 18 as described below, the inflatable balloon 14 is expanded from a deflated state (e.g., see deflated state of balloon 14 shown in FIG. 1B) to an inflated state (e.g., see partially inflated balloon 14 in FIG. 1A). The balloon 14 can be used alone or in combination with other inflatable balloons. The balloon 14 can be inflated sequentially or simultaneously with other balloons. The balloon 14 can also include additional inflation portions such as a separate inflation lumen that is in fluid communication with a separate balloon portion of the bifurcation delivery system 10. The balloon 14 can also include an inflatable bulge- or blister-type structure that extends radially outward from the body 26 of the balloon 14, such as the alternative inflatable portions disclosed in co-pending U.S. Published Patent Application Nos. 2005/0015108 and 2004/0138737, which applications are incorporated herein by reference.

Referring to FIGS. 1-5, the side branch locator 18 is shown mounted to an exterior surface of the inflatable balloon 14. In an alternative arrangement, the side branch locator 18 is mounted to the sheath 16. In this alternative arrangement, the inflatable balloon runs along a rail structure within the sheath to fix the relative rotated position of the balloon 14 to the sheath 16 while permitting axial movement of the sheath 16 relative to the balloon 14. Once the locator 18 is positioned in the branch vessel 4 of the vessel bifurcation 6, the sheath 16 can be retracted proximally while holding fixed the rotated position of the balloon 14.

The base 30 of the locator can include a contact surface for mounting to the balloon 14 (see FIG. 4). The contact surface is typically shaped to match the shape of an outer surface of that portion of the inflatable balloon 14 to which the base 30 is secured. The cross sectional shape and size of the locator 18 can be the same or change along a length of the locator 18 between the base 30 and the distal tip 34. FIG. 5A illustrates the moveable arm 32 having a circular cross section at a point along the length of arm 32 between the base 30 and distal tip 34. FIG. 5B illustrates an alternative rectangular cross sectional shape for the moveable arm 32.

The cross sectional shape and size of the moveable arm 32 can vary to alter the amount of flexibility of the moveable arm 32, which can be helpful in positioning the locator 18 within the branch vessel 4. The moveable arm 32 can have different cross-sectional shapes such as rectangular, circular, or oval shapes. The cross-sectional size of the moveable arm can vary depending on the cross sectional shape. In one example of a rectangular cross sectional shape, the moveable arm 32 has a thickness of about 50 to about 150 micrometers and a width that is about twice the thickness value. The length of the moveable arm can be, for example, about 1 to about 5 mm from the connection point of base 30 to the distal tip 34. The length can be determined based on the diameter of the main vessel and the diameter of the assembly 10 when the balloon 14 is deflated.

The base 30 can also have different shapes and sized. In one example, the base 30 has a generally rectangular shape with a width of about 200 to 400 micrometers and a thickness of about 50 to about 150 micrometers. The base 30 can have a contoured surface that matches a contoured shape of the balloon 14 exterior surface to which the locator 18 is mounted when the balloon 14 is inflated.

The illustrated example shows the locator 14 constructed with a preformed bend angle $\beta_R$ (see FIG. 3) when the side branch locator is in a rest state. The angle $\beta_R$ is usually defined between the moveable arm 32 and the contact surface of the base 30 that faces that portion of the inflatable balloon 14 to which the locator 18 is secured. Alternatively, the angle $\beta_R$ is defined between the outer surface of the inflatable balloon 14 to which the locator is secured and the moveable arm 32. The bend angle $\beta_R$ can be chosen to be substantially the same as an angle $\alpha$ at which the branch vessel 4 extends from the main vessel 2. For example, the angle $\beta_R$ can be in the range of about 50% to about 150% of the angle $\alpha$.

The restrained position of the moveable arm 32 is generally parallel to an outer surface of the balloon body 26 of the inflatable balloon 14. FIG. 1 illustrates the moveable arm 32 in the restrained position. The restrained position can vary depending on, for example, an internal size of the sheath 16, the inflated state of the inflatable balloon 14, and the flexibility of the sheath material.

Figure 3:
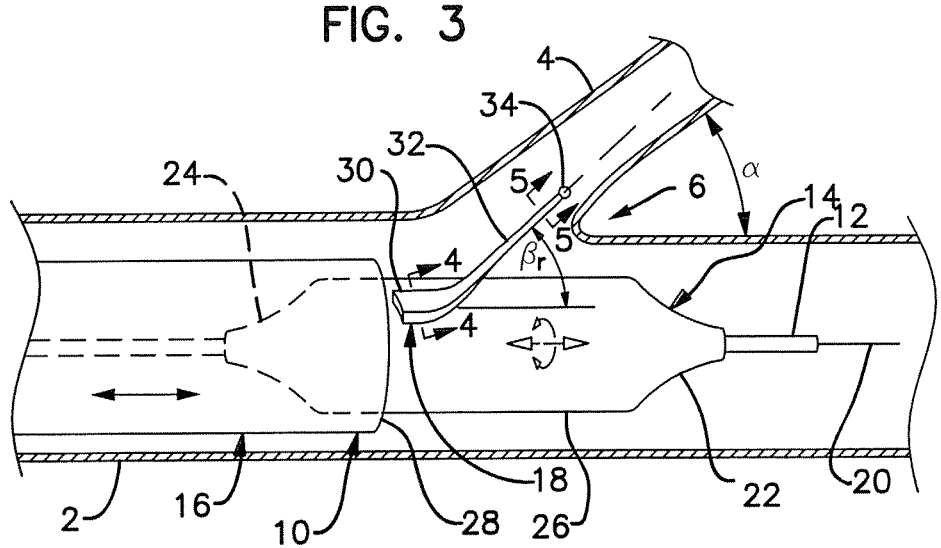
FIG. 3 is a schematic representation of the bifurcation delivery system shown in FIG. 1 with the side branch locator deployed within a side vessel branch.

The movement of moveable arm 32 between the restrained orientation shown in FIG. 1 and the extended position at the angle $\beta_R$ shown in FIG. 3 can occur automatically upon proximal retraction of the sheath 16. Automatic movement of the moveable arm 32 into the extended position can result from, for example, stored potential energy in the locator 18. The potential energy can be stored by forcing the locator into a shape different from its rest shape. When the locator is released from the different shape, the locator biases towards the rest shape. The embodiment of FIGS. 1-3 illustrates an example stored potential energy embodiment wherein the sheath 16 holds the moveable arm 32 in a restrained position different from the extended rest position shown in FIG. 3. Other example configurations that provide automatic movement of the moveable arm 32 are described in further detail below.

In some embodiments, movement of the moveable arm 32 can occur in response to a physical change or stimulus that does not occur automatically upon retraction of the sheath proximally from the locator 18. For example, the locator 18 can comprise a thermal shape memory material that returns to a preformed extended configuration upon heating above a threshold temperature. Example heat sources for heating of the thermal shape memory material include the patient's body and an electrical resistor. A bimetal material is another example material that could have shape memory properties when heated.

In another embodiment, the moveable arm 32 can move between the restrained and extended position using a current induced pseudo elastic material in the locator 18. A current induced material can change shape when stimulated with an electrical current. When a current induced pseudo-elastic material is included in, for example, the moveable arm of the locator 18, administering a small current to the pseudo-elastic material of the locator can change the shape of the locator to create movement of the moveable arm between the retained position of FIG. 1 to the extended position of FIG. 3. A potential benefit of using pseudo-elastic material is that the material can change back and forth between different shapes by changing the amount of current applied. Another potential benefit of using pseudo-elastic material is that it can be used without the sheath 16.

The side branch locator can include a thermal shape memory material such as Nitinol (Nickel Titanium Naval Ordnance Laboratory) that provides bimodal actuation. Thermal shape memory material provides for a change in shape of the object that includes the material. The change in shape includes a change from a new shape into an original shape by heating the material above a transition temperature. The transition temperature for thermal shape memory materials such as Flexinol® made by Dynalloy of Costa Mesa, Calif., is about 70° C. The transition temperature of other thermal shape memory materials can be higher or lower depending on the specific material composition. When a thermal shape memory material is cooled, it can be stretched or otherwise formed into a new shape different from the original shape. By including thermal shape memory material in the construction of the side branch locator 18, the original shape can be the extended configuration shown in FIG. 3, and the shape maintained when below the transition temperature is the retained configuration shown in FIG. 1. Using a thermal shape memory material can eliminate the need for the sheath 16 described herein. Alternatively, a thermal shape memory material can be used in combination with the sheath 16. A thermal shape memory material can also be used in combination with a fastener or a current induced material.

Some types of thermal shape memory material can be heated to its transition temperature with the body heat of the patient into which the stent delivery system is introduced. Using the body as the heating source, it is possible to estimate a range of time required to reach the transition temperature beginning with introduction of the stent delivery system into the patient. Reducing the initial temperature of the side branch locator before introducing the side branch locator into the patient (e.g., by refrigerating portions of the bifurcation delivery system) can help extend the time period required for reaching the transition temperature after the side branch locator has been introduced into the patient. The thermal shape memory material can also be heated using an electric current or other heat source besides the patient's body.

A sheath 16 is shown in the Figures as the structure used to hold the side branch locator in the restrained position. In alternative examples, other structure can be used to provide a similar function of holding the locator 18 in a restrained position. For example, a releasable fastener can be used to hold the locator in the restrained position, whereupon release of the fastener results in the locator 18 being permitted to move into the extended position.

In the illustrated example, at least some portions of the locator 18, such as the distal tip 34, preferably include a material that is visible under X-ray or in fluoroscopy procedures. A typical fluoroscopy procedure is operable by differentiating the absorption of X-rays by different material. Body materials such as carbon, oxygen and water typically have low X-ray absorption properties. Materials with high X-ray absorption are sometimes referred to as radiopaque materials. Some example radiopaque materials include gold, platinum, tantalum, and tungsten. Including a radiopaque material in the distal tip 34 can be particularly useful for tracking a position of the locator relative to the ostium of the branch vessel within a patient. Viewability of the side branch locator features can assist the physician operating the system 10 in more easily locating the branch vessel 4. An alternative to including radiopaque material in the features of locator 18 is to position radiopaque markers on the locator 18. In some embodiments, radiopaque markers can be secured to the distal tip 34, along a length of the moveable arm 32, to the base 30, or at any desired position on the expandable balloon 14 or catheter shaft 12.

An example of markers and marker arrangements for use with the example bifurcation treatment systems disclosed herein are described in U.S. Pat. No. 6,692,483 to Vardi, et al., and co-pending U.S. provisional patent application Ser. No. 60/776,149, filed on Feb. 22, 2006, and titled MARKER ARRANGEMENT FOR BIFURCATION CATHETER, which patent matters are incorporated herein by reference.

Another example side branch locator (not shown) includes more than one moveable arm each having a distinct distal tip 34. Alternatively, a single side branch locator with at least two moveable arms can include a common distal tip. In still further examples, multiple side branch locators can be used on with a single bifurcation treatment system, wherein each locator has at least one moveable arm. Each of the moveable arms in these examples can have a different size and shape and be positioned at different locations on the bifurcation treatment system. These and other example side branch locators can be useful for aligning the bifurcation treatment system relative to a branch vessel of a vessel bifurcation.

An exemplary manner of practicing aspects of the example system 10 and related methods will now be discussed with reference to FIGS. 1-9. First, the guidewire 20 is advanced within main vessel 2 to a position wherein a distal end of the guidewire 20 is positioned distally of the bifurcation 6. The catheter shaft 12 and inflatable balloon 14 along with the sheath 16 positioned over the locator 18 are advanced over the guidewire 20 into a position adjacent to the bifurcation 6 (see FIG. 1). Typically, the distal end 28 of the sheath 16 is first positioned distally of the side branch locator 18 in a first position prior to advancing the system 10 to the bifurcation 6. The sheath 16, when in the first position, retains the locator 18 in a non-deployed state within an interior of the sheath 16. The catheter shaft 12 is then adjusted both axially and radially to position the distal tip 34 of the side branch locator 18 distally of the bifurcation 6.

Referring now to FIG. 2, the sheath 16 is then retracted proximally to a position wherein the distal end 28 is proximal of at least the moveable arm 32 of the side branch locator 18. Retracting the sheath 16 allows the moveable arm 32 and distal tip 34 to extend radially outward from the inflatable balloon 14 into a deployed state. The moveable arm 32 extends radially outward either automatically or in response to a stimulus depending on the configuration of the locator 18. In the example of FIGS. 1-6, the locator 16 is adapted for automatic extension into an extended position upon being released from the sheath 16. When the moveable arm 32 extends away from the inflatable balloon 14, as shown in FIG. 2, the distal tip 34 engages an interior wall of the main vessel 2. Because the locator 14 has been positioned distally beyond the ostium of branch vessel 4, the distal tip 34 engages the sidewall of main vessel 2 at a location distally of the ostium of branch vessel 4 (see FIG. 2). The angle $\beta$ at which the moveable arm 32 extends relative to the balloon 14 when the moveable arm 32 is in contact with main vessel 2 is less than a rest angle $\beta_R$ (see FIG. 3). When the angle $\beta$ is less than $\beta_R$, the moveable arm 32 and distal tip 34 exert a biasing force radially outward upon the interior wall of the main vessel 2.

Referring now to FIG. 3, the locator 18 is then adjusted axially and radially until the distal tip 34 moves into the branch vessel 4. When the moveable arm 32 and distal tip 34 are exerting the radially outward directed biasing force described above, the side branch locator 18 tends to more actively move into the branch vessel 4 when the distal tip 34 is positioned in close proximity to the ostium of branch vessel 4.

The axial and radial movement of the catheter shaft 12 and inflatable balloon 14 can be done simultaneously or sequentially. In an example of sequential movement, a small axial movement can occur in the proximal direction followed by radial rotation, followed by a repeated sequence of these steps until the branch vessel 4 is located. In simultaneous movement, axial and radial adjustments are made at the same time until the locator 18 is positioned in branch vessel 4. Further axial movement of the sheath 16 in the proximal direction can be performed in order to ensure that the moveable arm 32 remains free from the sheath 16 when attempting to locate the locator 18 in the branch vessel 4.

In the event the physician is unable to position the distal tip 34 of the branch locator within the branch vessel 4 using the sequential or simultaneous movements described above, the sheath can be advanced in the distal direction relative to the inflatable balloon 14 to recapture the side branch locator 18 within the sheath 16 (see the arrangement of FIG. 1). The capability to reposition the locator 18 in a restrained position against the balloon 14 using the sheath 16 in the illustrated example, provides the physician with the ability to restart the procedure. The procedure is restarted after capturing the locator 18 within the sheath 16 by again advancing the bifurcation delivery system 10 distally to a position where the distal tip 34 of the locator 18 is positioned distally of the bifurcation 6. After proper repositioning of the locator 18 relative to the bifurcation 6, the sheath is retracted proximally to release the locator 18. The locator 18 can be moved axially and radially as necessary until the distal tip 34 of the locator is located in the branch vessel 4 (see FIGS. 1-3).

In another exemplary method of positioning locator 18 within the vessel branch 4, the guidewire 20 is advanced within main vessel 2 to a position wherein a distal end of the guidewire 20 is positioned distally of the vessel bifurcation 6, and the bifurcation delivery system is advanced over the guidewire 20 to a position where the locator 18 is positioned near the vessel bifurcation 6 but proximal of the ostium into branch vessel 4. The sheath 16 is then retracted proximally to permit the locator to move into a deployed state extending radially outward. The system 10 is then advanced distally and rotated until the locator 18 is positioned in the branch vessel 4.

After the side branch locator 18 is positioned with the distal tip 34 advanced into branch vessel 4, the bifurcation treatment system 10 can be used to perform treatment of the bifurcation 6. In one example treatment, the sheath 16 is removed and a stent 40 is advanced over the catheter shaft 12 and inflatable balloon 14 into alignment with the branch vessel 4 (see FIG.

Figure 7:
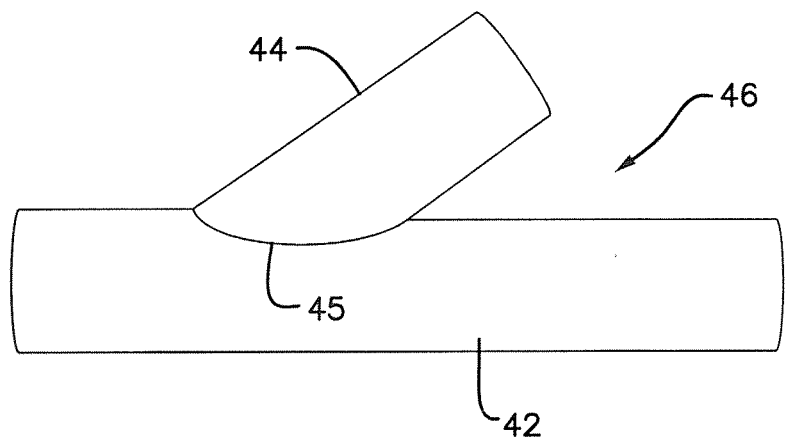
FIG. 7 is a schematic side view of the stent shown in FIG. 6.
Figure 8:
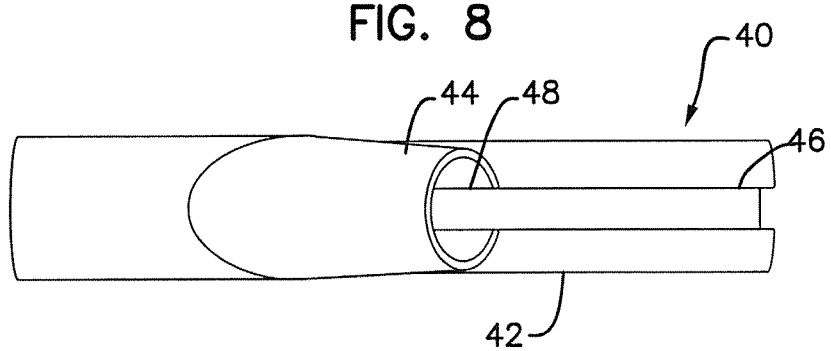
FIG. 8 is a schematic top view of the stent shown in FIG. 6.
Figure 9:
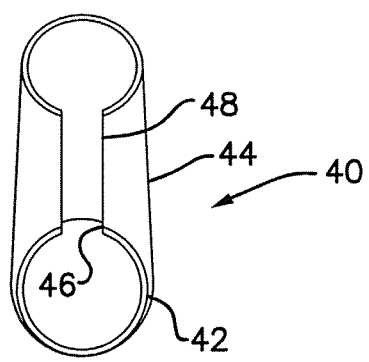
FIG. 9 is a schematic front view of the stent shown in FIG. 6.

6). The stent 40 includes a main body 42 having an access slot 46, and a branch extension 44 having an access slot 48. The slots 46, 48 together define a continuous open path through which the side branch locator 18 can pass as the stent 40 is advanced in the distal direction. Aligning the locator 18 within the slots 46, 48 typically results in alignment of the branch extension 44 with the branch vessel 4. FIGS. 7-9 further illustrate the features of stent 40.

The stent 40 can be adjusted both axially and radially in order to align the side branch locator 18 within the slots 46, 48. When the stent 40 is aligned with the branch vessel 4, the inflatable balloon 14 can be inflated to expand the main body 42 of the stent 40 for treatment of the main vessel 2. The inflatable balloon 14 can include additional inflatable portions such as balloons and inflation lumens to expand the stent 40 and treat the vessel bifurcation 6.

Additional inflation members (e.g., inflatable balloons) and expansion members (e.g., stent structures) can be advanced through the branch extension 44 and into the branch vessel 4, wherein the additional inflation and expansion members are used to further treat the branch vessel 4. For example, a specially shaped balloon catheter can be advanced through the stent 40 and into the branch vessel 4 for use in aligning the branch extension 44 relative to the side branch 4. In another example, the distal tip 34 of the locator 18 includes an inflatable balloon that can be inflated after locating the distal tip 34 within the branch vessel 4 (e.g., see inflated balloon tip 34 in FIG. 11).

Alternative bifurcation delivery system embodiments are configured for use with stents that include self-expanding features. Such alternative delivery systems typically do not require the same type of expandable balloons described above for expansion of the stent 40. Further, such alternative delivery systems can include side branch locators that are positioned directly on the catheter shaft rather than on an expandable balloon.

Referring now to FIGS. 7-9, the branch portion 44 of the stent 40 can be integrally formed as a single piece with main body 42. In other embodiments, the branch extension 44 can be a separate member that is connected to the main body 42 at a connection point or seam 45. The connection point or seam 45 can include, for example, a weld connection, an adhesive connection, or a fastener connection for securing the branch extension 44 to the main body 42.

III. The Example Illustrated in FIGS. 10-11

Referring now to FIGS. 10-11, an example bifurcation delivery system 10 having an alternative stent 240 is shown and described. The stent 240 has a generally tubular, cylindrical shape. A side opening 250 is defined in a sidewall of the stent between distal and proximal ends 241, 242 of the stent 240. The system 10 is assembled with the locator 18 positioned on the inflatable balloon 14, and the moveable arm 32 and distal tip 34 extending through the opening 250. The moveable arm 32 is shown in FIG. 11 in a non-deployed state in a generally restrained position maintained by the sheath 16. The sheath 16 is advanced distally over the stent 240 and locator 18 until the distal end 28 of the sheath 16 is positioned distally of the distal tip 34 of the locator 18. In other configurations, the moveable arm 32 can be held in the restrained position as a result of the materials used in the locator 18 rather than being restrained by stent 16. For example, the locator 18 can comprises thermal shape memory material that returns to a preformed extended configuration upon heating above a threshold temperature. Alternatively, the locator 18 can include a current-induced pseudo elastic material that upon stimulated with a current causes the moveable arm 32 to move into an extended position.

FIG. 10 illustrates the sheath 16 retracted proximally to permit the moveable arm 32 to extend radially outward into a deployed state. After the locator 18 released and extended radially outward, the catheter shaft 12 and inflatable balloon 14 can be adjusted axially and radially until the distal tip 34 of the locator 18 is positioned in the branch vessel 4 as shown in FIG. 10.

IV. The Example Illustrated in FIG. 12

Figure 12:
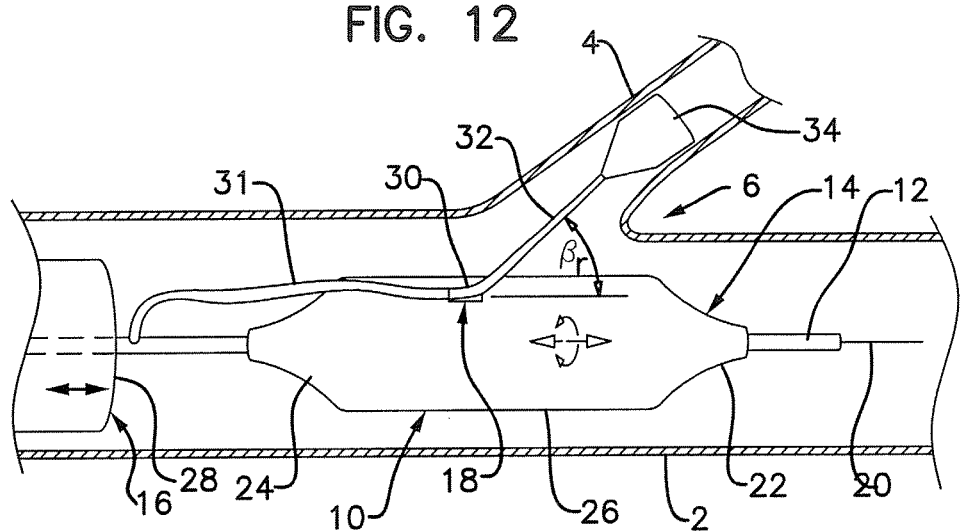
FIG. 12 is a schematic representation of another example bifurcation delivery system having a side branch locator with an expandable distal tip.

Referring now to FIG. 12, an example bifurcation delivery system 10 having an alternative features for the side branch locator 18 is shown and described. The locator 18 includes a distal tip 34 having inflation capabilities. The distal tip 34 is shown coupled to an inflation lumen 31 via the base 30 and moveable arm 32 of the locator 18. Alternatively, the inflation lumen 31 can extend to the distal tip 34 independent of the base 30 and moveable arm 32. The inflation lumen 31 is typically in fluid communication with a source of inflation fluid that can be used to inflate the distal tip 34 after the distal tip 34 has been positioned within the branch vessel 4. When the distal tip 34 is inflated sufficiently to engage the internal walls of the branch vessel 4, the locator 18 can align the system 10 relative to the branch vessel 4.

While the example illustrated in FIG. 12 does not include a stent, a stent having, for example, the configurations described above with reference to the examples shown in FIGS. 1-12 can be used with the inflatable distal tip 34.

IV. Summary and Conclusion

One aspect of the present disclosure relates to a catheter assembly that includes a catheter having a distal end, an inflatable balloon member positioned at the distal end of the catheter shaft, and a locator member. The locator member has a first end secured to the inflatable balloon member and a second end that is moveable from a retracted position adjacent to the inflatable balloon member to an extended position spaced apart from the inflatable balloon member.

Another aspect of the present disclosure relates to a medical stent delivery system. The system includes a catheter shaft, a locator member, and a stent. The locator member has a fixed end and a moveable end, and is configured to move between a retracted position and an extended position. The stent includes a lateral branch opening located at a position between distal and proximal open ends of the stent. The second end of the locator member extends through the lateral branch opening.

A further aspect of the present disclosure relates to a method of locating a branch vessel of a vessel bifurcation. The method includes positioning a guidewire in a main vessel of the vessel bifurcation, the guidewire having a distal end positioned distally of the vessel bifurcation. The method also includes advancing a catheter assembly over the guidewire to the vessel bifurcation. The catheter assembly includes a catheter shaft having a distal end portion, an inflatable balloon member extending from the distal end portion of the catheter shaft, and a branch locator. The branch locator has a first end secured to the inflatable balloon member and a second end moveable relative to the inflatable balloon member. The method further includes moving the second end of the branch locator from a retracted position arranged adjacent to the inflatable balloon member to an extended position spaced apart from the inflatable balloon member and extending toward the branch vessel. The method can also include adjusting radial and axial positions of the catheter assembly relative to the branch vessel until the second end of the branch locator extends into the branch vessel.

It is noted that not all of the features characterized herein need to be incorporated within a given arrangement, for the arrangement to include improvements according to the present disclosure.

We claim:

1. A catheter assembly, comprising:
   (a) a catheter shaft having a distal end;
   (b) an inflatable balloon member positioned at the distal end of the catheter shaft; and
   (c) an elongate locator member having first and second ends and a length extending therebetween, the first end secured directly to the inflatable balloon member and the second end moveable from a retracted position adjacent to the inflatable balloon member to an extended position spaced apart from the inflatable balloon member, wherein when in the retracted position, the length of the elongate locator member extends along the balloon with the second end positioned distal of the first end.

2. The assembly of claim 1, further comprising a sheath, the sheath having proximal and distal ends and defining a lumen, the sheath moveable from a first position surrounding a portion of the inflatable balloon member and the locator member to a second position wherein the distal end of the sheath is positioned proximal of the locator member to permit the locator member to move into the extended position.

3. The assembly of claim 2, further comprising a stent positioned around the inflatable balloon member, wherein a portion of the sheath in the first position is located at a position between the stent and the locator member.

4. The assembly of claim 1, wherein the locator member includes a thermal shape memory material.

5. The assembly of claim 1, wherein the locator member includes a current induced pseudo elastic material.

6. The assembly of claim 1, wherein the locator member includes a distal tip, the distal tip including an inflatable portion.

7. The assembly of claim 1, further comprising a stent having a lateral branch opening positioned at location between distal and proximal open ends of the stent, wherein the locator member extends through the lateral branch opening.

8. A medical stent delivery system, comprising:
   (a) a catheter shaft;
   (b) an elongate locator member having a secured end and a moveable end and a length extending therebetween, the locator member configured to move between a retracted position and an extended position;
   (c) an inflatable balloon member extending from a distal end of the catheter shaft, the inflatable balloon member having a longitudinal axis, wherein the secured end of the locator member is secured directly to the inflatable balloon, wherein when in the retracted position, the length of the elongate locator member extends along the longitudinal axis with the moveable end positioned distal of the secured end; and
   (d) a stent having a lateral branch opening located at a position between distal and proximal open ends of the stent, the moveable end of the locator member extending through the lateral branch opening.

9. The system of claim 8, further comprising a sheath defining an internal cavity, the sheath moveable between a first position wherein at least a portion of the locator member is positioned within the cavity to hold the locator member in the retracted position, and a second position wherein the locator member is removed from the cavity.

10. The system of claim 8, wherein the stent includes an aperture extending from the lateral branch opening to the distal open end of the stent.

* * * * *